United States Patent [19]

Hilverda

[11] Patent Number: Plant 5,545

[45] Date of Patent: Aug. 27, 1985

[54] CARNATION NAMED HILKARI

[75] Inventor: Jan J. Hilverda, Aalsmeer, Netherlands

[73] Assignee: Hilverda B.V., Aalsmeer, Netherlands

[21] Appl. No.: 559,358

[22] Filed: Dec. 8, 1983

[51] Int. Cl.[3] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new carnation plant of the spray type distinguished by its relatively small flowers of a light pink coloration which are produced continuously and profusely on long flower stems borne on a tall, spray type bush having a rapid growth rate, abundant foliage, and reaching a height of about one meter.

1 Drawing Figure

BACKGROUND OF THE NEW PLANT

My new variety of spray carnation plant was discovered by me in 1977 as a seedling resulting from my crossing of selected unnamed seedlings with the object of producing new varieties having a higher yield and improved quality, this new plant having been found among a group of similarly produced seedlings in greenhouse at Aalsmeer, The Netherlands. This new plant was selected by me for propagation because of its profuse production of quite delicate pink flowers grown on relatively long flower stems borne on a tall bush. Propagation of this plant was done by me at Aalsmeer by means of cuttings and such propagation was carried on through several generations, which demonstrated that the distinctive characteristics of this new variety hold true from generation to generation and appear to be firmly fixed.

DESCRIPTION OF THE DRAWING

My new spray type carnation plant is illustrated by the accompanying photographic drawing which shows the color characteristics of the flower, the form of the flower stem and a face view of a fully opened flower, together with parts of a partially opened bud, the photographic reproduction of the flower color being as nearly true as is reasonably possible to obtain by conventional photographic procedures.

DESCRIPTION OF THE NEW PLANT

The following is a detailed description of my new variety of carnation plant based upon observations of greenhouse grown plants made early in 1983 at Aalsmeer, The Netherlands, the color designations being according to The R.H.S. Colour Chart published by The Royal Horticultural Society of London, England.

THE PLANT

Origin: Seedling.

Parentage:

*Seed parent.*—Selected unnamed seedling.

*Pollen parent.*—Selected unnamed seedling.

Classification:

*Botanic.*—*Dianthus caryophyllus.*

*Commercial.*—Spray carnation.

Form: Bush of tall spray type.

Height: About one meter.

Growth habit: Strong, sturdy and upright with alternate branching.

Foliage:

*Quantity.*—Abundant.

*Size of leaf.*—Approximately 11 cm. long.

*Shape of leaf.*—Sessile, lanceolate with acuminate tip.

*Texture.*—Leathery.

*Color.*—Upper side — Blue Green. Under side — Blue Green.

*Leaflets.*—None.

THE BUD

Form: Inverted pear shape.

Size: Small to medium.

*Diameter.*—About 10 to 12 mm.

*Length.*—About 20 to 28 mm.

Rate of opening: With mature bud, the flower will open about five days later.

Color:

*When sepals first divide.*—Light pink to pink.

*When petals begin to unfurl.*—Pink.

Sepals: Hooded over the bud until dividing.

*Shape.*—Generally ovate with acute apex. Sepals stand up when petals unfurl.

*Color.*—Inside — Light Green. Outside — Dark Green.

Calyx:

*Size.*—Medium.

*Shape.*—Funnel-shaped and long pointed.

*Aspect.*—Smooth.

*Splitting.*—The calyx does not split.

Peduncle:

*Length.*—About 10 mm.

*Character.*—Erect and rigid.

*Color.*—Dark Green.

THE FLOWER

Blooming habit: Profuse and continuous.

Size of bloom: Small.

*Diameter.*—About 50 to 55 mm.

*Depth.*—About 25 to 30 mm.

Borne: As cluster with more than three flowers per stem.

Shape: When bloom first opens, high centered. As bloom matures, it tends to flatten.

Petalage:

*Number of petals.*—33.

*Arrangement.*—Imbricated.
*Form.*—Fan-shaped with irregular dentate to crenate margins.
*Color.*—Outer Petal — 48D. Inside Petal — 48D.
*Texture.*—Soft.
*Appearance.*—Velvety.

Petaloids: About 33 in number.
*Size.*—About 35 mm. long and 20 mm. wide.
*Color.*—48D.

Flower stem:
*Length.*—About 50 to 60 cm.
*Color.*—Blue green to dark green.
*Character.*—Sturdy and upright.

Persistence: Petals hang on and dry.

Fragrance: Weak.

Lasting quality:
*As a cut flower.*—10 to 16 days.

REPRODUCTIVE ORGANS

Stamens:
*Anthers.*—Number: Many. Arrangement: Normal. Length: About 4 mm. Color: Straw yellow.

*Filaments.*—Length: About 10 to 12 mm. Color: Light green.
*Pollen.*—Color: White.

Pistils:
*Number.*—Two.
*Styles.*—Length: About 12 mm. Color: Green to light green.
*Stigmas.*—Color: White.

Ovaries: Cylindrical in shape.
*Color.*—Pale yellow to cream to white.

This new plant most nearly resembles "Silvery Pink". The new plant is more compact, however, and more vigorous in its growth habit, it has a darker shade of pink and somewhat shorter stems.

I claim:

1. The new and distinct variety of spray carnation, substantially as herein shown and described, characterized in particular by its delicate pink flower color, its profuse and continuous blooming habit, and the rapid growth rate of its tall, spray shape bush with relatively long flower stems.

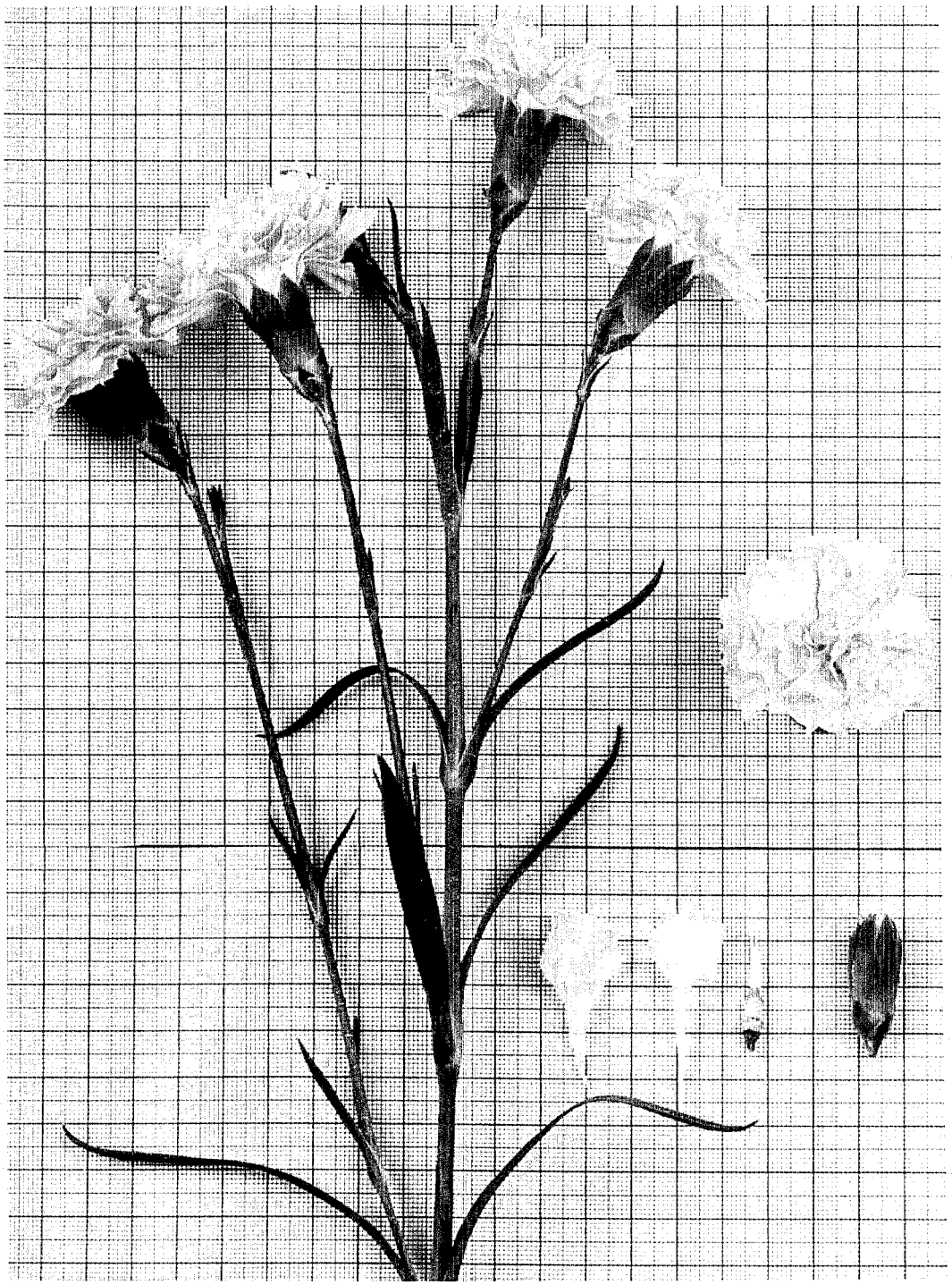

* * * * *